US010857351B2

(12) United States Patent
Wang et al.

(10) Patent No.: US 10,857,351 B2
(45) Date of Patent: Dec. 8, 2020

(54) LEAD ANCHORS FOR ELECTRICAL STIMULATION LEADS AND SYSTEMS AND METHODS OF MAKING AND USING

(71) Applicant: Boston Scientific Neuromodulation Corporation, Valencia, CA (US)

(72) Inventors: Kevin Peng Wang, Fremont, CA (US); Jacob B. Leven, Huntington Beach, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 224 days.

(21) Appl. No.: 15/961,346

(22) Filed: Apr. 24, 2018

(65) Prior Publication Data

US 2018/0311494 A1    Nov. 1, 2018

Related U.S. Application Data

(60) Provisional application No. 62/491,904, filed on Apr. 28, 2017.

(51) Int. Cl.
*A61N 1/05*    (2006.01)

(52) U.S. Cl.
CPC ......... *A61N 1/0558* (2013.01); *A61N 1/0529* (2013.01)

(58) Field of Classification Search
CPC ............... A61N 1/0558; A61N 1/0529; A61N 2001/0582
See application file for complete search history.

(56) References Cited

U.S. PATENT DOCUMENTS

| 376,810 A | 1/1888 | Brill |
|---|---|---|
| 612,685 A | 10/1898 | Thorp et al. |
| 2,046,837 A | 7/1936 | Phillips |
| 3,866,615 A | 2/1975 | Hewson |
| 4,141,752 A | 2/1979 | Shipko |
| 4,276,882 A | 7/1981 | Dickhudt et al. |
| 4,316,471 A | 2/1982 | Shipko et al. |
| 4,462,401 A | 7/1984 | Burgio |

(Continued)

FOREIGN PATENT DOCUMENTS

| EP | 85417 A1 | 8/1983 |
|---|---|---|
| EP | 0597213 A1 | 5/1994 |

(Continued)

*Primary Examiner* — Rex R Holmes
(74) *Attorney, Agent, or Firm* — Lowe Graham Jones PLLC; Bruce E. Black

(57) ABSTRACT

A lead anchor includes a lead passageway defined along a central body and configured to receive a lead. The central body includes a twistable region that reversibly twists and stretches. First and second hubs are coupled to opposing ends of the central body. The first hub is rotatable relative to the second hub about the central body. Rotation of the first hub relative to the second hub causes twisting of the twistable region. When a lead is inserted into the lead passageway and the twistable region is twisted into a twisted configuration the central body compresses against the lead to retain the lead within the lead passageway. A locking mechanism transitions the hubs between an unlocked position, where the first hub is rotatable relative to the second hub, and a locked position, where the hubs resist rotation relative to one another.

12 Claims, 8 Drawing Sheets

(56) References Cited

U.S. PATENT DOCUMENTS

| | | |
|---|---|---|
| 4,632,670 A | 12/1986 | Mueller, Jr. |
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |
| 5,158,097 A | 10/1992 | Christlieb |
| 5,228,248 A | 7/1993 | Haddock |
| 5,269,809 A | 12/1993 | Hayhurst et al. |
| 5,370,662 A | 12/1994 | Stone et al. |
| 5,376,108 A | 12/1994 | Collins et al. |
| 5,484,445 A | 1/1996 | Knuth |
| 5,584,874 A | 12/1996 | Rugland et al. |
| 5,628,780 A | 5/1997 | Helland et al. |
| 5,746,722 A | 5/1998 | Pohndorf et al. |
| 5,865,843 A | 2/1999 | Baudino |
| 5,895,360 A | 4/1999 | Christopherson et al. |
| 5,957,968 A | 9/1999 | Belden et al. |
| 6,175,710 B1 | 1/2001 | Kamaji et al. |
| 6,181,969 B1 | 1/2001 | Gord |
| 6,192,279 B1 | 2/2001 | Barreras, Sr. et al. |
| 6,224,450 B1 | 5/2001 | Norton |
| 6,360,750 B1 | 3/2002 | Gerber et al. |
| 6,473,654 B1 * | 10/2002 | Chinn ............. A61N 1/05 600/375 |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,895,280 B2 | 5/2005 | Meadows et al. |
| 6,901,287 B2 | 5/2005 | Davis et al. |
| 6,978,180 B2 | 12/2005 | Tadlock |
| 6,984,145 B1 | 1/2006 | Lim |
| 7,069,083 B2 | 6/2006 | Finch et al. |
| 7,072,719 B2 | 7/2006 | Vinup et al. |
| 7,161,461 B1 | 1/2007 | Nelson |
| 7,184,841 B1 | 2/2007 | Bodner et al. |
| 7,203,548 B2 | 4/2007 | Whitehurst et al. |
| 7,235,078 B2 | 7/2007 | West, Jr. |
| 7,244,150 B1 | 7/2007 | Brase et al. |
| 7,343,202 B2 | 3/2008 | Mrva et al. |
| 7,402,076 B1 | 7/2008 | Lim |
| 7,437,193 B2 | 10/2008 | Parramon et al. |
| 7,447,546 B2 | 11/2008 | Kim et al. |
| 7,450,997 B1 | 11/2008 | Pianca et al. |
| 7,596,414 B2 | 9/2009 | Whitehurst et al. |
| 7,610,102 B2 | 10/2009 | Kowalczyk |
| 7,610,103 B2 | 10/2009 | Whitehurst et al. |
| 7,672,734 B2 | 3/2010 | Anderson et al. |
| 7,761,165 B1 | 7/2010 | He et al. |
| 7,783,359 B2 | 8/2010 | Meadows |
| 7,787,960 B2 | 8/2010 | Lubenow |
| 7,792,590 B1 | 9/2010 | Pianca et al. |
| 7,809,446 B2 | 10/2010 | Meadows |
| 7,848,803 B1 | 12/2010 | Jaax et al. |
| 7,853,321 B2 | 12/2010 | Jaax et al. |
| 7,860,568 B2 | 12/2010 | Deininger et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,224,451 B2 | 7/2012 | Jaax et al. |
| 8,229,573 B2 | 7/2012 | Chen et al. |
| 8,271,094 B1 | 9/2012 | Moffitt et al. |
| 8,295,944 B2 | 10/2012 | Howard et al. |
| 8,301,268 B1 * | 10/2012 | Jones ............. A61N 1/057 607/126 |
| 8,315,704 B2 | 11/2012 | Jaax et al. |
| 8,364,278 B2 | 1/2013 | Pianca et al. |
| 8,391,985 B2 | 3/2013 | McDonald |
| 8,412,349 B2 | 4/2013 | Barker |
| 8,483,845 B2 | 7/2013 | Sage |
| 8,568,462 B2 | 10/2013 | Sixto et al. |
| 8,688,232 B2 | 4/2014 | Finley et al. |
| 8,688,235 B1 | 4/2014 | Pianca et al. |
| 9,265,935 B2 | 2/2016 | Thacker |
| 9,433,755 B2 | 9/2016 | Behymer et al. |
| 2001/0000187 A1 | 4/2001 | Peckham et al. |
| 2002/0107554 A1 | 8/2002 | Biggs et al. |
| 2003/0074023 A1 | 4/2003 | Kaplan et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0033393 A1 | 2/2005 | Daglow |
| 2005/0165465 A1 | 7/2005 | Pianca et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0205995 A1 | 9/2006 | Browning |
| 2006/0206162 A1 | 9/2006 | Wahlstrand et al. |
| 2007/0010794 A1 | 1/2007 | Dann et al. |
| 2007/0050005 A1 | 3/2007 | Lauro |
| 2007/0078399 A1 | 4/2007 | Olson |
| 2007/0100348 A1 | 5/2007 | Cauthen et al. |
| 2007/0150036 A1 | 6/2007 | Anderson |
| 2007/0219595 A1 | 9/2007 | He |
| 2007/0255369 A1 | 11/2007 | Bonds et al. |
| 2008/0071320 A1 | 3/2008 | Brase |
| 2008/0091255 A1 | 4/2008 | Caparso et al. |
| 2008/0140130 A1 | 6/2008 | Chan et al. |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0196939 A1 | 8/2008 | Lubenow et al. |
| 2008/0228251 A1 | 9/2008 | Hill |
| 2008/0243220 A1 | 10/2008 | Barker |
| 2008/0275401 A1 | 11/2008 | Sage et al. |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0187222 A1 | 7/2009 | Barker |
| 2009/0198312 A1 | 8/2009 | Barker |
| 2009/0210043 A1 | 8/2009 | Reddy |
| 2009/0254151 A1 | 10/2009 | Anderson et al. |
| 2009/0259260 A1 | 10/2009 | Bentley et al. |
| 2009/0270940 A1 | 10/2009 | Deininger |
| 2009/0276021 A1 | 11/2009 | Meadows et al. |
| 2009/0281571 A1 | 11/2009 | Weaver et al. |
| 2009/0281576 A1 | 11/2009 | Weaver et al. |
| 2009/0281579 A1 | 11/2009 | Weaver et al. |
| 2010/0076535 A1 | 3/2010 | Pianca et al. |
| 2010/0094425 A1 | 4/2010 | Bentley et al. |
| 2010/0174240 A1 | 7/2010 | Wells et al. |
| 2010/0268298 A1 | 10/2010 | Moffitt et al. |
| 2010/0274336 A1 | 10/2010 | Nguyen-Stella et al. |
| 2010/0286670 A1 | 11/2010 | Doyle et al. |
| 2010/0312319 A1 | 12/2010 | Barker |
| 2011/0004267 A1 | 1/2011 | Meadows |
| 2011/0005069 A1 | 1/2011 | Pianca |
| 2011/0022066 A1 | 1/2011 | Sevrain |
| 2011/0022142 A1 | 1/2011 | Barker et al. |
| 2011/0060395 A1 | 3/2011 | Cantlon |
| 2011/0078900 A1 | 4/2011 | Pianca et al. |
| 2011/0130817 A1 | 6/2011 | Chen |
| 2011/0130818 A1 | 6/2011 | Chen |
| 2011/0178573 A1 | 7/2011 | Nguyen-Stella et al. |
| 2011/0238129 A1 | 9/2011 | Moffitt et al. |
| 2011/0264180 A1 | 10/2011 | Hamilton |
| 2011/0313500 A1 | 12/2011 | Barker et al. |
| 2012/0016378 A1 | 1/2012 | Pianca et al. |
| 2012/0035692 A1 * | 2/2012 | Cantlon ............. A61N 1/0558 607/116 |
| 2012/0046710 A1 | 2/2012 | Digiore et al. |
| 2012/0071949 A1 | 3/2012 | Pianca et al. |
| 2012/0150202 A1 | 6/2012 | Chen et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |

(56) References Cited

U.S. PATENT DOCUMENTS

| | | |
|---|---|---|
| 2012/0203320 A1 | 8/2012 | DiGiore et al. |
| 2012/0203321 A1 | 8/2012 | Moffitt et al. |
| 2012/0232626 A1 | 9/2012 | Daglow |
| 2012/0277670 A1 | 11/2012 | Goetz |
| 2012/0283835 A1 | 11/2012 | Bentley et al. |
| 2012/0316615 A1 | 12/2012 | Digiore et al. |
| 2012/0330355 A1 | 12/2012 | Finley et al. |
| 2013/0105071 A1 | 5/2013 | Digiore et al. |
| 2013/0149031 A1 | 6/2013 | Changsrivong |
| 2013/0197602 A1 | 8/2013 | Pianca et al. |
| 2013/0204336 A1 | 8/2013 | Sharma |
| 2013/0238023 A1 | 9/2013 | Wales et al. |
| 2014/0074093 A9 | 3/2014 | Nelson et al. |
| 2014/0155936 A1* | 6/2014 | Lee .................. A61N 1/0558 606/232 |
| 2014/0180345 A1 | 6/2014 | Chan et al. |
| 2014/0343645 A1 | 11/2014 | Wechter |
| 2015/0005856 A1 | 1/2015 | Pianca et al. |
| 2015/0045865 A1 | 2/2015 | Nageri et al. |
| 2015/0051674 A1 | 2/2015 | Barner et al. |
| 2015/0051675 A1 | 2/2015 | Barner |
| 2015/0066121 A1 | 3/2015 | Govea et al. |
| 2015/0246216 A1 | 9/2015 | Barker |
| 2015/0343198 A1 | 12/2015 | Nageri et al. |
| 2016/0256679 A1 | 9/2016 | Nguyen-Stella et al. |
| 2017/0036013 A1 | 2/2017 | Leven |
| 2017/0246454 A1 | 8/2017 | Leven |

FOREIGN PATENT DOCUMENTS

| | | |
|---|---|---|
| JP | H07-014681 | 3/1995 |
| JP | 2001339829 A | 12/2001 |
| WO | 1998033551 A1 | 8/1998 |
| WO | 1999/053994 | 10/1999 |
| WO | 2000/013743 A2 | 3/2000 |
| WO | 2000/064535 | 11/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010/126853 A1 | 11/2010 |
| WO | 2012151356 A1 | 11/2012 |
| WO | 2013112920 A1 | 8/2013 |

* cited by examiner

LEAD ANCHORS FOR ELECTRICAL STIMULATION LEADS AND SYSTEMS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/491,904, filed Apr. 28, 2017, which is incorporated herein by reference.

FIELD

The present invention is directed to the area of implantable electrical stimulation systems and methods of making and using the systems and, in particular, to implantable electrical stimulation systems that include lead anchors for anchoring leads to patient tissue, as well as methods of making and using the leads, lead anchors, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to central body tissue.

BRIEF SUMMARY

One embodiment is a lead anchor that includes a central body having a longitudinal length with a first end portion and an opposing second end portion; a lead passageway defined along the entire longitudinal length of the central body, the lead passageway configured and arranged to receive a lead; a twistable region extending along at least a portion of the longitudinal length of the central body with the lead passageway extending therethrough, the twistable region configured and arranged for reversibly twisting and stretching along the longitudinal length of the central body; a first hub coupled to the central body along the first end portion of the central body; a second hub coupled to the central body along the second end portion of the central body; and a locking mechanism. The first hub is rotatable relative to the second hub about the central body. The rotation of the first hub relative to the second hub causes a corresponding twisting of the twistable region from an untwisted configuration into a twisted configuration. When a lead is inserted into the lead passageway and the twistable region is twisted into the twisted configuration the central body compresses against an outer surface of the lead to retain the lead within the lead passageway. The locking mechanism includes at least one locking member configured and arranged to transition the first hub and the second hub between an unlocked position where the first hub is rotatable relative to the second hub and a locked position where the first hub and the second hub resist rotation relative to one another.

In at least some embodiments, the at least one locking mechanism is configured and arranged to transition the first hub and the second hub from the unlocked position to the locked position by physical engagement of the first hub and the second hub using the at least one locking member. In at least some embodiments, the locking mechanism is configured and arranged to transition the first hub and the second hub from the locked position to the unlocked position by physical disengagement of the at least one locking member from at least one of the first hub or the second hub. In at least some embodiments, the at least one locking member includes pins disposed externally to the central body.

In at least some embodiments, the at least one locking member includes a central tube disposed concentrically over the central body. In at least some embodiments, the locking mechanism includes locking-member-engagement surfaces disposed along the at least one locking member and hub-engagement surfaces disposed along each of the first hub and the second hub, and where the first hub and the second hub resist rotation relative to one another when the locking-member-engagement surfaces interlock with the hub-engagement surfaces. In at least some embodiments, the locking-member-engagement surfaces include at least one of a notch or a tab and the hub-engagement surfaces include at least one of a notch or a tab that interlocks with the at least one notch or tab of the locking-member-engagement surfaces. In at least some embodiments, the central tube includes a first interlocking member coupled to the first hub and comprising a first engagement surface; and a second interlocking member coupled to the second hub and comprising a second engagement surface with a shape that interlocks with the first engagement surface; where the central tube is configured and arranged for transitioning the first hub and the second hub from the unlocked position to the locked position when the first engagement surface interlocks with the second engagement surface. In at least some embodiments, the first engagement surface includes at least one of a projection or a recess and the second engagement surface comprises at least one of a projection or a recess that interlocks with the at least one of a projection or a recess of the first engagement surface. In at least some embodiments, the first engagement surface includes at least one of a knob or a groove and the second engagement surface comprises at least one of a knob or a groove that interlocks with the at least one of a knob or a groove of the first engagement surface. In at least some embodiments, the central tube defines at least one slot to facilitate flexing and bending and providing strain relief.

In at least some embodiments, the twistable region is disposed entirely between the first hub and the second hub. In at least some embodiments, the twistable region includes at least one bump to provide localized resistance against patient tissue.

In at least some embodiments, the lead anchor further includes at least one protruding feature attached to the central body and defining an eyelet configured and arranged for receiving a suture. In at least some embodiments, the lead anchor further includes at least one suture channel disposed at least partially around a circumference of the central body and aligned axially along the longitudinal length of the central body with the at least one protruding feature.

Another embodiment is an implantable stimulation arrangement that includes the lead anchor described above and an electrical stimulation lead with an electrode array, where the lead anchor is configured and arranged for receiving a portion of the electrical stimulation lead and removably retaining the received portion of the electrical stimulation lead.

Yet another embodiment is an implantable stimulation device that includes the lead anchor described above; an electrical stimulation lead with an electrode array, where the lead anchor is configured and arranged for receiving a portion of the electrical stimulation lead and removably retaining the received portion of the electrical stimulation lead; and a control module coupleable to the electrical stimulation lead.

Still yet another embodiment is a method of anchoring a lead. The method includes providing the lead anchor described above; advancing an electrode array of an electrical stimulation lead into a patient to a target stimulation location; sliding the lead anchor along the electrical stimulation lead to a desired placement position along the electrical stimulation lead with a portion of the electrical stimulation lead disposed within the lead lumen of the lead anchor; twisting the twistable region to hold the lead in position relative to the lead anchor; and transitioning the locking mechanism to the locked position to prevent the twistable region from untwisting.

In at least some embodiments, the method described above further includes transitioning the locking mechanism of the lead anchor to the unlocked position prior to twisting the twistable region.

In at least some embodiments, twisting the twistable region to hold the lead in position relative to the lead anchor includes rotating the first hub relative to the second hub about the longitudinal length of central body of the lead anchor In at least some embodiments, sliding the lead anchor along the electrical stimulation lead includes sliding the lead anchor along the electrical stimulation lead while the twistable region of the lead anchor is in the untwisted configuration.

In at least some embodiments, twisting the twistable region to hold the lead in position relative to the lead anchor includes rotating at least one of the first hub or the second hub relative to the other about the longitudinal length of central body of the lead anchor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems and, in particular, to implantable electrical stimulation systems that include lead anchors for anchoring leads to patient tissue, as well as methods of making and using the leads, lead anchors, and electrical stimulation systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244, 150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
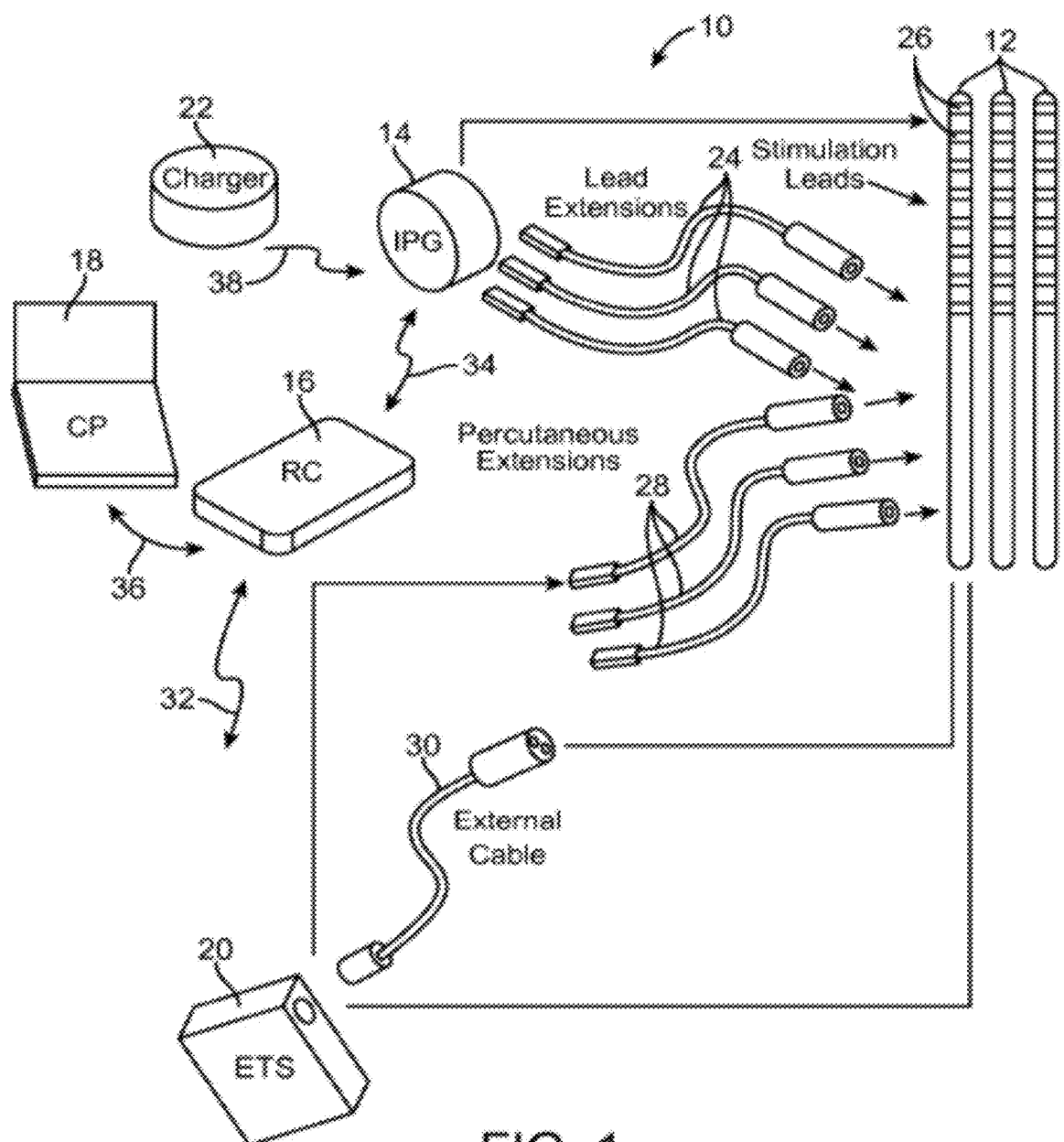
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's central body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2A:
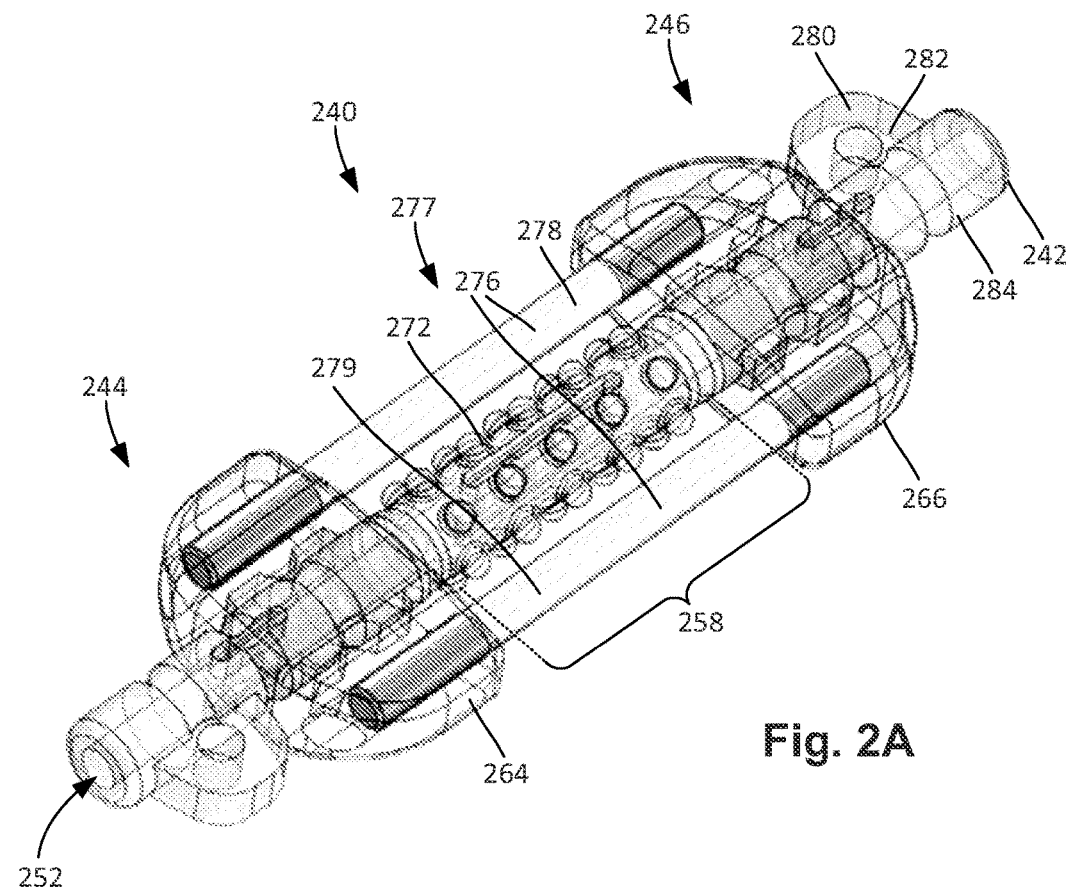
FIG. 2A is a schematic perspective view of one embodiment of a lead anchor suitable for use with the lead or lead extension of FIG. 1, according to the invention.
Figure 2B:
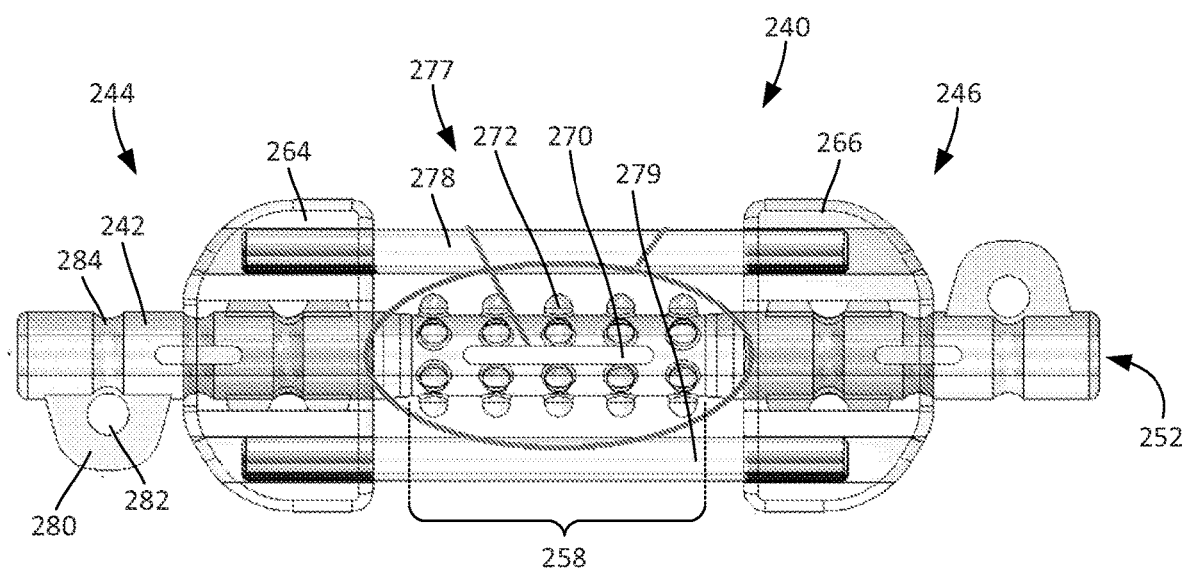
FIG. 2B is a schematic top view of one embodiment of the lead anchor of FIG. 2A, according to the invention.

Turning to FIGS. 2A-2B, a lead anchor can be used in an implantable device, such as an implantable spinal cord stimulator or any other stimulator system, to anchor a lead or lead extension to patient tissue. The lead anchor will be described herein as anchoring a lead, but it will be understood that the lead anchor can also anchor a lead extension within the patient's central body.

The lead anchor includes a lead passageway that can be twisted and locked in a twisted configuration to retain a portion of the lead within the lead anchor. FIGS. 2A-2B illustrate one embodiment of a lead anchor 240 which includes a central body 242 with a first end portion 244 and an opposing second end portion 246. FIG. 2A shows the lead anchor 240 in perspective view. FIG. 2B shows the lead anchor 240 in top view.

The central body 242 defines a lead passageway 252, which provides a continuous passageway through the central body 242 between the first end portion 244 and the second end portion 246. The lead passageway 252 is dimensioned to receive a portion of a lead, such as the lead (12 in FIG. 1), from either of the first end portion 244 or the second end portion 246. The lead passageway 252 receives the lead such that the lead typically extends from both the first end portion 244 and the second end portion 246 when the lead is anchored with the lead anchor 240. The lead anchor can be positioned at any suitable location along the longitudinal length of the lead. In the case of percutaneous leads, the lead anchor can be slid onto the lead from either the distal end or the proximal end of the lead.

The central body 242 may have any suitable shape including, for example, oblong, rectangular, cylindrical, elliptical, or the like, or any other regular or irregular shape, or the like. In at least some embodiments, one or more of the end portions 244, 246 of the central body 242 are elongated. In at least some embodiments, one or more of the end portions 244, 246 are tapered. The length and tapering of the end portions 244, 246 can be the same or can be different for the two ends.

The central body 242 includes a twistable region 258 disposed along the central body 242 with a portion of the lead passageway extending therethrough. The twistable region 258 is flexible enough to be twistable and stretchable along the longitudinal length of the central body 242. The twistable region 258 can extend along the entire longitudinal length of the central body 242, or less than the entire longitudinal length of the central body 242.

The central body 242 is flanked by a first hub 264 and a second hub 266. The first hub 264 is disposed along the first end portion 244 of the central body 242 and the second hub 266 is disposed along the second end portion 246 of the central body 242. In at least some embodiments, the lead passageway extends through at least one of the hubs 264, 266. In the illustrated embodiment, the lead passageway is shown extending through both hubs 264, 266. In some embodiments, the hubs 264, 266 are disposed at the ends of the lead anchor 240. In other embodiments, as illustrated in FIGS. 2A-2B, the central body 242 extends laterally from the hubs 264, 266 (i.e., one or more of the hubs 264, 266 may be inset from the ends of the lead anchor).

The hubs 264, 266 are rotatable relative to one another about the longitudinal length of the central body. The first hub 264 is attached to the central body 242 such that rotation of the first hub 264 relative to the second hub 266 causes the twistable region 258 to twist (or untwist). Similarly, the second hub 266 is attached to the central body such that rotation of the second hub 266 relative to the first hub 264 also causes the twistable region 258 to twist (or untwist). Twisting of one of the hubs relative to the other can cause the twistable region 258 to transition between an untwisted configuration and a twisted configuration. When the twistable region 258 is in the untwisted configuration, a lead (e.g., lead 12 in FIG. 1) is extendable though the lead passageway 252 and able to slide (e.g., move axially relative to the lead anchor 240) along the lead passageway 252. When the twistable region 258 is in the twisted configuration, an inner diameter of the lead passageway 252 along the twisted region 258 is reduced enough from the twisting to cause the central body 242 to compress against an outer surface of an inserted lead and grip or otherwise hold (e.g., resist axial and rotational movement of) the lead relative to the lead anchor 240.

Optionally, the central body 242 may define one or more slits, such as slit 270, extending along, or approximately along, a longitudinal length of the twistable region 258 for facilitating twisting. The slit(s) separate the twistable region 258 into strips which fall inward when twisted around a lead. The slit(s) may help isolate the twistable region 258 that is intended to twist from other portions of the central body, as well as facilitate easier twisting and easier contracting of the twistable region 258 onto an inserted lead.

Optionally, one or more bumps, such as bump 272 are disposed along an outer surface of the twistable region 258 to provide localized resistance against patient tissue. It will be understood that in some embodiments, such as shown in FIGS. 2A-4D, the twistable region may directly contact patient tissue during implantation, while in other embodiments, such as shown in FIGS. 5A-7B, the twistable region does not directly contact patient tissue during implantation.

The twistable region 258 is formed from a material suitable for being stretched and twisted. The twistable region 258 is also sufficiently rigid to grip or otherwise hold an inserted lead when in the twisted configuration, yet also capable of being deformed or flexed when twisted, to assume the twisted configuration. In at least some embodiments, the twistable region 258 is formed as a polymer-based, semi-rigid central tube suitable for implantation. The twistable region 258 can be formed, for example, from silicone. The twistable region 258 can be formed from other materials in lieu of, or in addition to silicone including, for example, polyvinyl chloride, polyurethane, silicone, thermoplastic polyesters, polycarbonate fluoropolymers, and the like.

In at least some embodiments, the twistable region 258 has a durometer of, or approximately, 50. In at least some embodiments, the twistable region 258 has a durometer of, or approximately, 60. In at least some embodiments, the twistable region 258 has a durometer no less than 50 and no greater than 60. In at least some embodiments, the twistable region 258 has a durometer no less than 45 and no greater than 65. The twistable region 258 can be extruded or molded based, at least in part, on which features are preferred. Slitting can be done post-extrusion. Molding may be a better option when complex features (e.g., slits, bumps, eyelets, suture channels, or the like) are desired.

In at least some embodiments, the twistable region 258 is formed from the same material as the remaining portions of the central body. The twistable region 258 may, in some instances, be formed with a reduced thickness from remaining portions of the central body to increase flexibility of the twistable region compared to the remaining portions of the central body. One or more additives may be added to increase the flexibility of the twistable region compared to other portions of the central body. In alternate embodiments, the twistable region 258 is formed from different material as the remaining portions of the body. In at least some alternate embodiments, the twistable region 258 is formed as a coiled spring.

The hubs 264, 266 can be formed from the same material as the central body, or from different material as the central body. In at least some embodiments, at least one of the central body 242 or the hubs 264, 266 is formed by a molding process. The hubs 264, 266 and the central body 242 can be molded together, or the hubs can be overmolded separately to control the stiffness of the hubs. It may be advantageous for the hubs 264, 266 to be stiffer than the twistable region to facilitate gripping and twisting of the hubs, as well as to facilitate repeated and reliable locking (as discussed below).

It may be useful to be able to maintain the twistable region 258 in either the twisted position or the untwisted position to prevent undesired twisting or untwisting. For example, it may be desirable to maintain the twistable region 258 in the untwisted configuration when placing the lead. It may also be desirable to maintain the twistable region 258 in the twisted configuration while anchoring the lead.

Accordingly, the lead anchor 240 includes a locking mechanism 276 configured and arranged for enabling the first hub 264 and the second hub 266 to be transitioned between an unlocked position and a locked position. When the hubs 264, 266 are in the unlocked position, at least one of the first hub 264 or the second hub 266 is rotatable relative to the other about the longitudinal length of the central body. When the hubs 264, 266 are in the locked position, the first hub 264 and the second hub 266 resist rotation relative to the other.

The locking mechanism 276 includes one or more locking members 277 that engage the hubs, thereby causing the hubs to maintain a particular rotation relative to one another. Maintaining the particular relative rotation of the hubs requires that the engagement of the locking member(s) 277 to the hubs be robust enough to withstand the rotational force of the twistable region 258 when the twistable region is in the twisted configuration. In at least some embodiments, the locking members engage the hubs along interlocking surfaces.

The locking members illustrated in FIGS. 2A-2B include pins 278 and 279 that span the twistable region 258 and physically engage the first hub 264 and the second hub 266. In the illustrated embodiment, the pins 278, 279 are disposed external to the central body 242. The pins 278, 279 can be removably attachable to one of the two hubs 264, 266, while being either permanently or removably attachable to the other of the two hubs 264, 266. The locking mechanism 276 illustrated in FIGS. 2A-2B uses apertures defined in the hubs 264, 266 into which ends of the pins 246, 648 extend during engagement to prevent rotation of the hubs 264, 266 relative to one another when the ends of the pins 278, 279 are inserted into the apertures. In some embodiments, the pins 278, 279 are affixed in their respective apertures of one of the hubs 264, 266.

In some instances, it may be desirable to anchor the lead anchor 240 to patient tissue. Accordingly, the central body 242 can include one or more optional protruding features 280 with eyelets 282 for receiving a suture, a staple, or the like, for securing the lead anchor 240 to patient tissue. The protruding features 280 may be circumferentially and axially disposed at any suitable location around the central body 242. In at least some embodiments, the protruding features 280 with eyelets 282 are circumferentially offset by 180° from one another (or disposed on opposite sides of the central body 242) as illustrated in FIGS. 2A-2B. In at least some embodiments, the protruding features 280 are also axially or longitudinally offset from each other as illustrated in FIGS. 2A-2B. The lead anchor 240 can include any suitable number of protruding features 280 including, for example, one, two, three, four, five, six, seven, eight, or more protruding features 280. The protruding features 280 may be made from either the same material or different material from the central body 242. In at least some embodiments, at least one of the protruding features 280 is disposed medially, with respect to the longitudinal length of the central body 242, from one of the hubs 264, 266 such that the hub 264, 266 is disposed between the protruding feature 280 and the twistable region 258. In at least some embodiments, at least one of the protruding feature 280 is disposed along at least one of the hubs 264, 266. It may be advantageous to arrange the protruding features 280 on an end of the lead anchor that causes the lead anchor to compress during pushing/pulling of the lead anchor during implantation to prevent undesired separation of the hubs and a corresponding undesired transition between a locked position and an unlocked position, or vice versa.

In at least some embodiments, the central body 242 includes one or more optional suture channels 284 that are disposed at least partially around a circumference of the central body 242. In at least some embodiments, a suture channel 284 is also axially-aligned with one or more of the protruding features 280 and eyelets 282, as illustrated in FIGS. 2A-2B. The suture channels 284 facilitate suturing of the lead anchor 240 to patient tissue by enabling sutures to be disposed around the central body 242 and passed through one or more of the eyelets 282 without increasing the diameter of the lead anchor 240, while also preventing (or reducing the likelihood of) the sutures from slipping off an end of the central body 242.

Figure 3A:
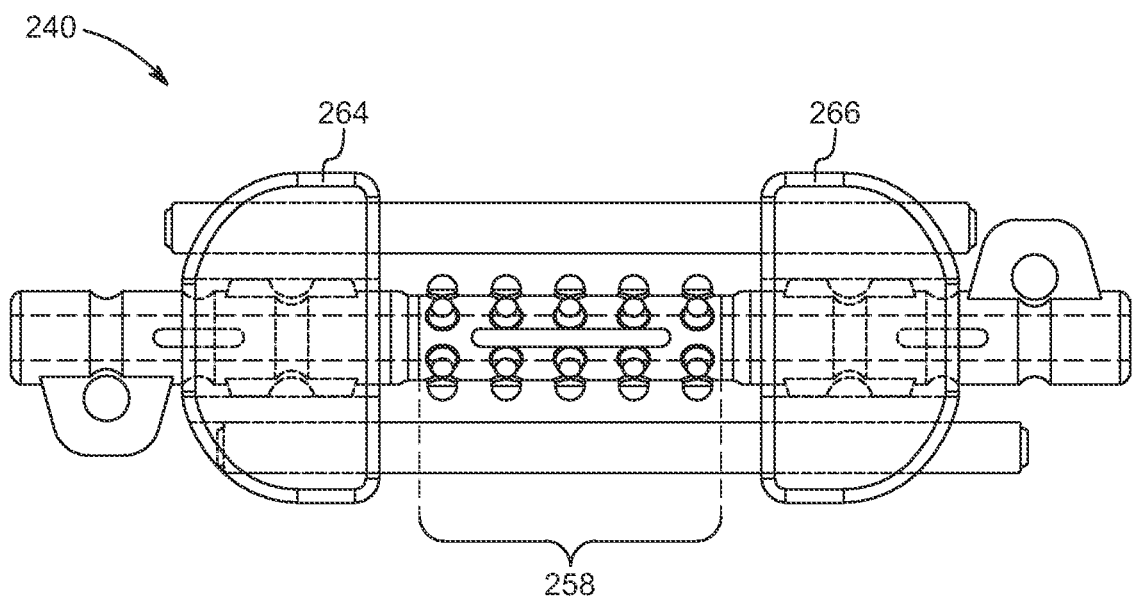
FIG. 3A is a schematic top view of one embodiment of the lead anchor of FIGS. 2A-2B in a locked position and an untwisted configuration, according to the invention.

FIG. 3A is a schematic top view of one embodiment of the lead anchor 240 in a locked position with the twistable region 258 in an untwisted configuration. As mentioned above, when the twistable region 258 is in the untwisted configuration, a lead (e.g., lead 12 in FIG. 1) is extendable though the lead passageway and able to slide axially relative to the lead anchor.

Figure 3B:
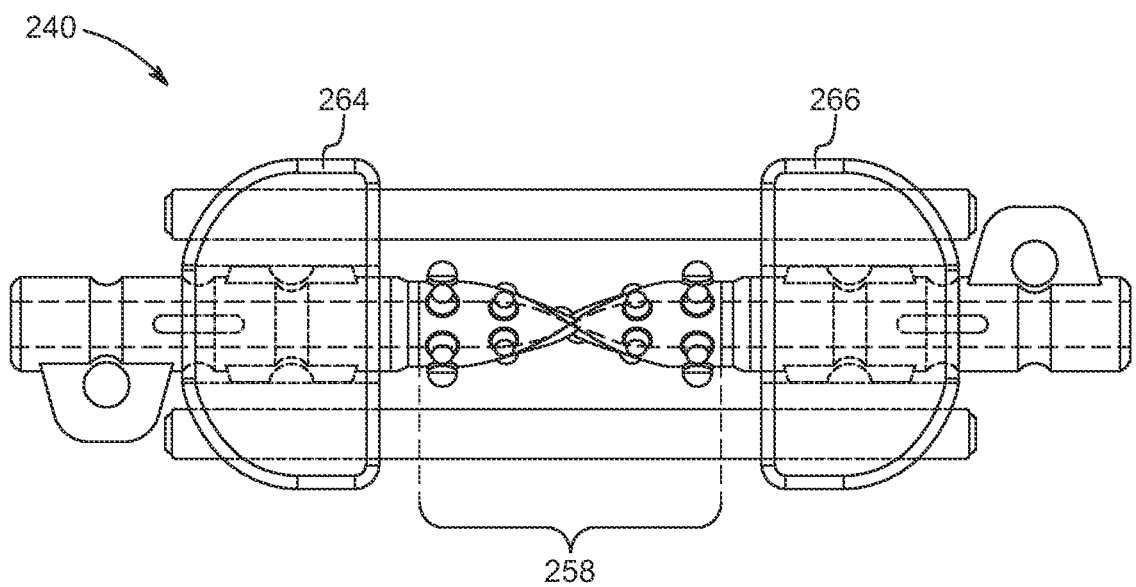
FIG. 3B is a schematic top view of one embodiment of the lead anchor of FIG. 3A in a locked position and a twisted configuration, according to the invention.

FIG. 3B is a schematic top view of one embodiment of the lead anchor 240 in a locked position with the twistable region 258 in a twisted configuration. When the twistable region 258 is in the twisted configuration, an inner diameter of the lead passageway along the twisted region is reduced by an amount sufficient to cause the lead anchor to compress against an outer surface of an inserted lead and resist axial and rotational movement of the lead relative to the lead anchor.

Transitioning the twistable region 258 between the untwisted configuration and the twisted configuration is performed by rotating one of the hubs 264, 266 relative to the other while the hubs 264, 266 are in the unlocked position. Once the twistable region 258 is in the desired configuration, the hubs 264, 266 can be placed in the locked position, as illustrated in FIGS. 3A-3B, to resist undesired twisting/untwisting.

Transitioning the hubs 264, 266 from a locked position to an unlocked position can be performed by stretching the twistable region 258 by an amount sufficient to disengage the locking member (e.g., the pins) from at least one of the hubs. In at least some embodiments, stretching the twistable region 258 can be performed by pulling the hubs 264, 266 apart from one another along the longitudinal length of the central body. Conversely, transitioning the hubs 264, 266 from an unlocked position to a locked position can be performed by stretching the twistable region 258 by an amount sufficient to engage the locking member with both hubs.

The hubs 264, 266 can be pulled apart and/or rotated relative to one another by a user, either by hand or a hand-held tool. The hubs 264, 266 can be rotated relative to one another by: rotating the first hub 264 and not the second hub 266; rotating the second hub 266 and not the first hub 264; rotating both the hubs 264, 266 in opposing directions; or rotating both hubs 264, 266 by different amounts in the same direction.

The number of twists needed to transition the twistable region from an untwisted configuration to a twisted configuration (i.e., twisted sufficiently to retain an inserted lead) can vary depending on the difference between the diameter of the lead passageway along the twistable region and the diameter of the inserted lead. Other factors that may affect the number of twists needed to transition the twistable region from an untwisted configuration to a twisted configuration include the stretchability and/or thickness of the material used to form the twistable region, temperature, humidity, and the like.

In at least some embodiments, the number of relative rotations between the hubs 264, 266 sufficient to retain an inserted lead is one-quarter revolutions, one-half revolutions, three-quarter revolutions, one revolution, one-and-a-quarter revolutions, one-and-a-half revolutions, one-and-a-three-quarter revolutions, two revolutions, two-and-a-half revolutions, three revolutions, three-and-a-half revolutions, four revolutions, five revolutions, or more.

In the illustrated embodiments, the pins 278, 279 engage with the hubs 264, 266 in half-revolution increments. It will be understood that the locking mechanism can be configured to enable smaller increments by increasing the number of pins. For example, four pins could be used, where the pins are each offset by 90 degrees when viewing the lead anchor along an axis transverse to the longitudinal length of the central body. It may be advantageous to use two pins because using additional pins (e.g., 4 pins) may increase the profile of the lead anchor from the 2-pin embodiment.

Turning to FIGS. 4A-4D, when the first hub and the second hub are in the unlocked position, the twistable region can be twisted from an untwisted configuration to a twisted configuration. In at least some embodiments, when the first hub and the second hub are in the unlocked position, the twistable region of the central body can be untwisted from a twisted configuration to an untwisted configuration. In some instances, the twistable region can be repeatedly twisted and untwisted, as desired, when the hubs are in the unlocked position.

When the twistable region is in the untwisted configuration a lead is extendable though the lead passageway and able to move axially relative to the lead anchor, and when the twistable region is in the twisted configuration the inner diameter of the lead passageway extending through the twisted region reduces enough to cause the central body of the lead anchor to compress against an outer surface of an inserted lead and resist axial and rotational movement of the lead relative to the lead anchor.

Figure 4A:
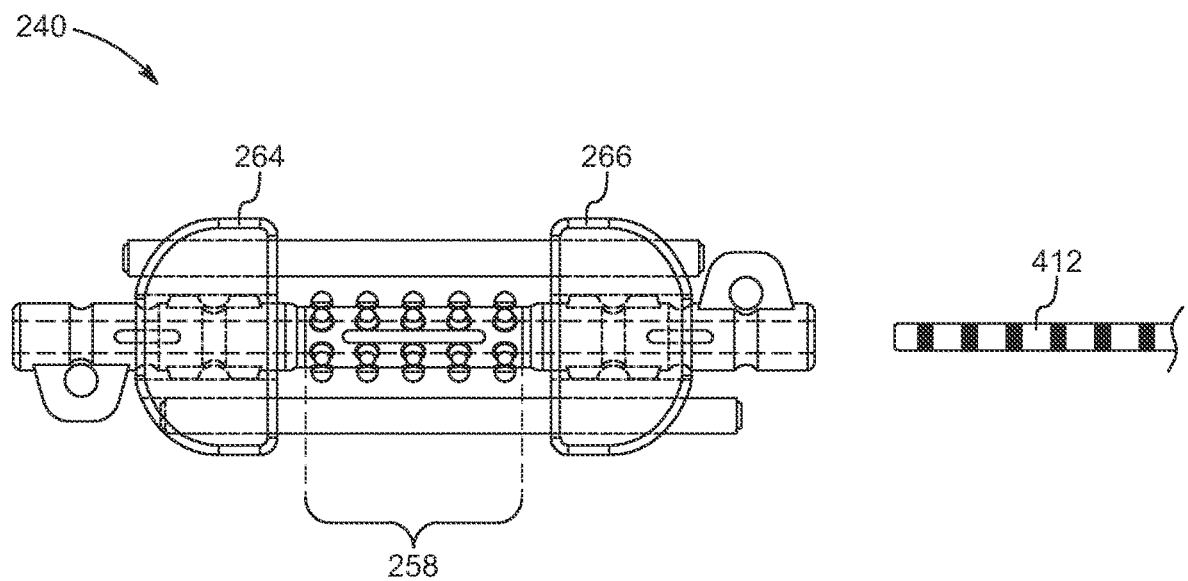
FIG. 4A is a schematic top view of one embodiment of the lead anchor of FIGS. 2A-3B in a locked position and an untwisted configuration and a distal portion of a lead suitable for being received and retained by the lead anchor, according to the invention.
Figure 4B:
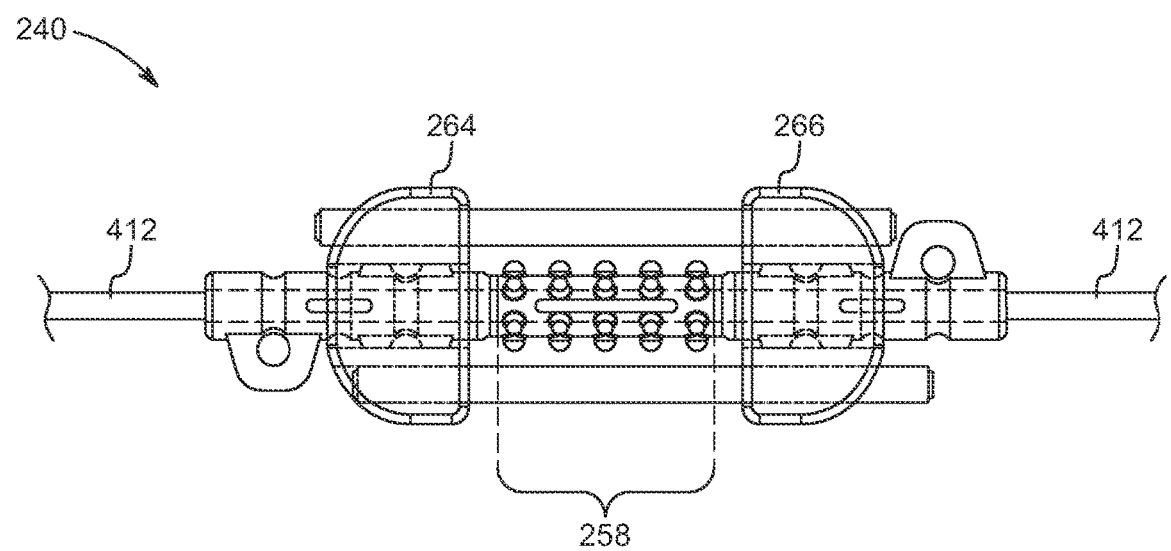
FIG. 4B is a schematic top view of one embodiment of the lead of FIG. 4A received by the lead anchor of FIG. 4A, with the lead anchor in a locked position and an untwisted configuration, according to the invention.

FIGS. 4A-4D illustrate one embodiment of a method of anchoring a lead to the lead anchor. FIG. 4A is a schematic top view of one embodiment of the lead anchor 240 with the hubs 246, 266 in the locked position and the twistable region 258 disposed in an untwisted configuration. A distal portion of a lead 412 is positioned in proximity to the lead anchor 240. FIG. 4B shows the lead 412 received by the lead passageway of the lead anchor 240. The hubs 246, 266 are in the locked position and the twistable region 258 remains in an untwisted configuration. The lead 412 can be moved axially relative to the lead anchor 240 until the lead anchor 240 is disposed over a desired portion of the lead 412.

Once the lead anchor is disposed over a desired portion of the lead 412, the lead anchor can be transitioned to a twisted configuration (e.g., by relative rotation of the hubs) to anchor the lead to the lead anchor. The hubs are unlocked (e.g., by pulling the hubs apart to disengage the locking members) prior to twisting the twistable region. The hubs can be unlocked prior to positioning the lead along the lead anchor. However, it may be an advantage to leave the lead anchor in a locked position until the lead anchor 240 is disposed over a desired portion of the lead 412 to ensure that the twistable region remains untwisted.

Figure 4C:
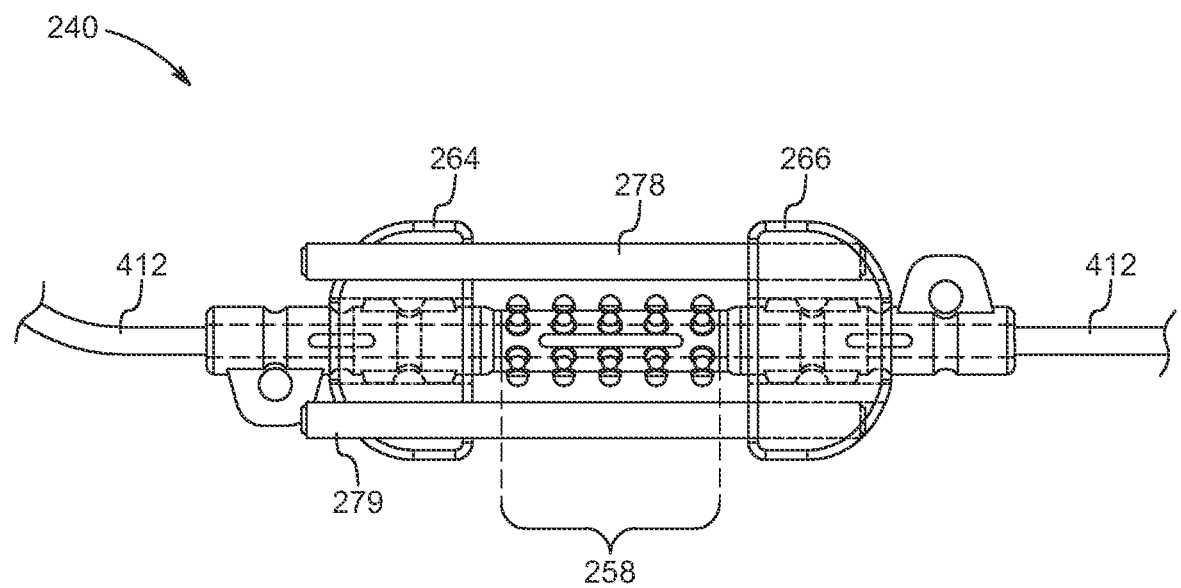
FIG. 4C is a schematic top view of one embodiment of the lead of FIG. 4B received by the lead anchor of FIG. 4B, with the lead anchor in an unlocked position and an untwisted configuration, according to the invention.

FIG. 4C shows the hubs 246, 248 unlocked from one another and the twistable region in an untwisted configuration. As shown in FIG. 4C, the pins 278, 279 have been disengaged from the hub 264, while remaining engaged with the hub 266. In some embodiments, the pins 278, 279 can be disengaged from both hubs 264, 266. In alternate embodiments, the pins 278, 279 are permanently attached to one of the hubs (e.g., hub 266). The hubs 264, 266 can be transitioned to the unlocked position by pulling one, or both, of the hubs axially-away from the other by a sufficient amount to enable the pins 278, 279 to be disengaged from one of the hubs 264, 266. The axial stretchability of the twistable region enables, at least in part, the pins 278, 279 to be removed from one of the hubs 264, 266.

Figure 4D:
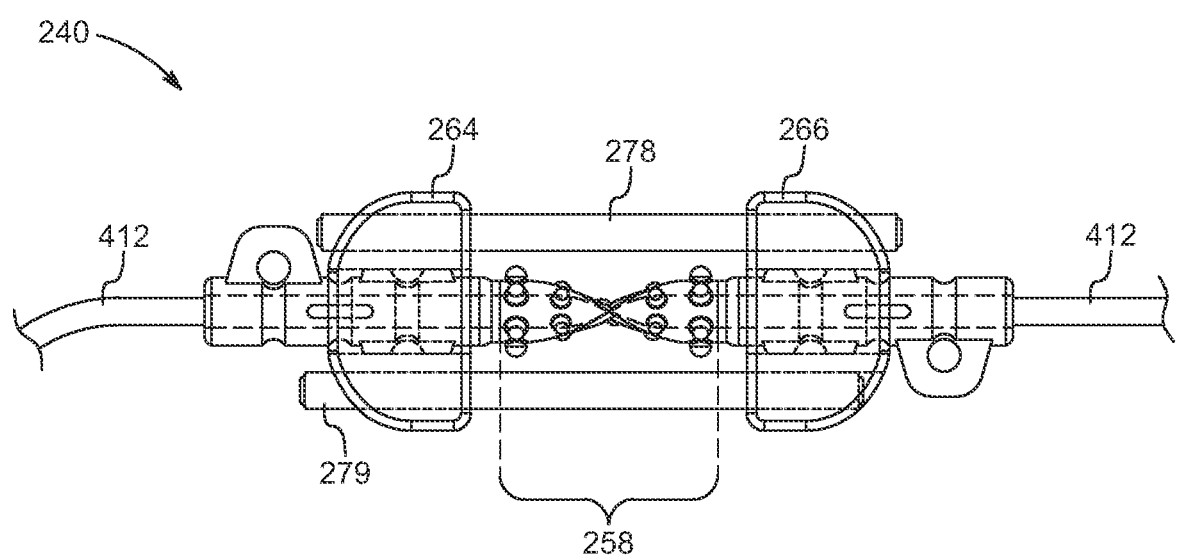
FIG. 4D is a schematic top view of one embodiment of the lead of FIG. 4C received by the lead anchor of FIG. 4C, with the lead anchor in a locked position and a twisted configuration, according to the invention.

Once the hubs 246, 248 are in the unlocked position, the hubs 246, 248 can be rotated relative to each other until the lead is retained by the twistable region and the pins 278, 279 can be re-engaged with the hub from which they were previously disengaged, thereby transitioning the hubs to the locked position. FIG. 4D shows the twistable region 258 in the twisted configuration to retain the lead and the pins 278, 279 engaged with the hub 264 to lock the hubs 246, 248 in the locked position, thereby resisting axial or rotational movement of the lead 412 relative to the lead anchor 240.

Figure 5A:
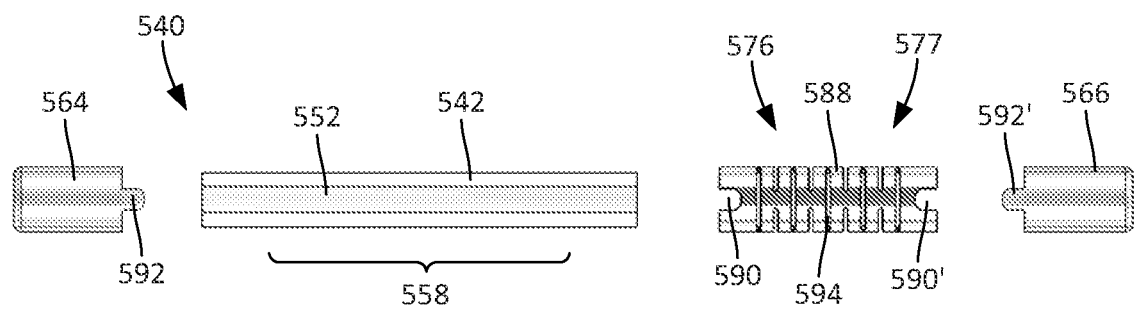
FIG. 5A is a schematic exploded view of an alternate embodiment of a lead anchor suitable for use with the lead or lead extension of FIG. 1, according to the invention.
Figure 5B:
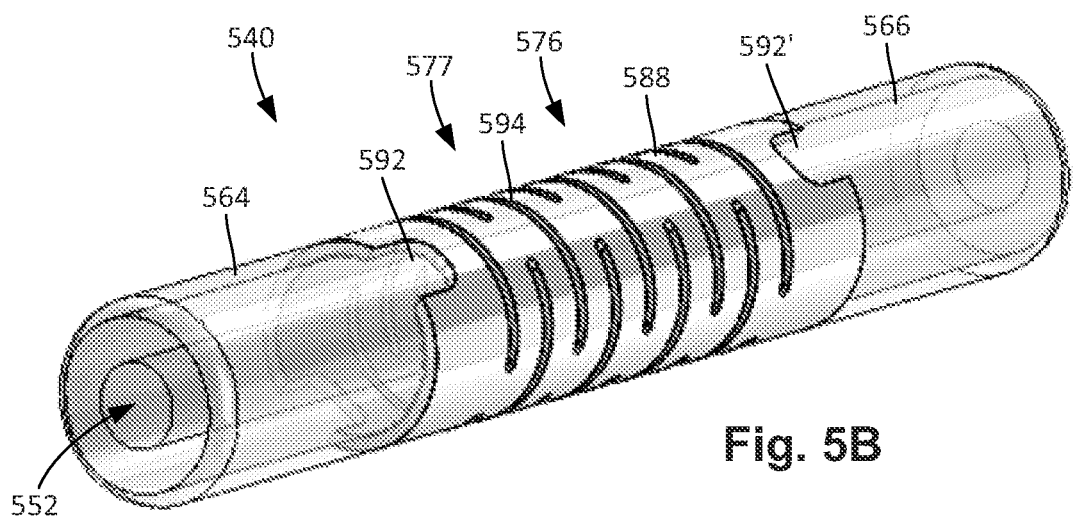
FIG. 5B is a schematic perspective view of one embodiment of the lead anchor of FIG. 5A, according to the invention.
Figure 5C:
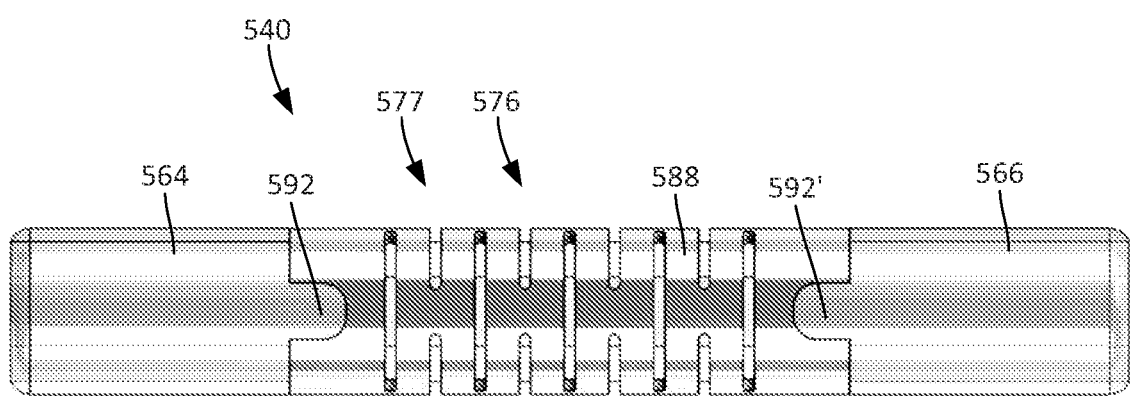
FIG. 5C is a schematic side view of one embodiment of the lead anchor of FIG. 5A, according to the invention.

The lead anchor can be formed with alternate types of locking members in addition to, or in lieu of, pins. FIGS. 5A-5C illustrates a second embodiment of a lead anchor 540 suitable for anchoring to a lead. FIG. 5A shows the lead anchor 540 in exploded side view. FIG. 5B shows the lead anchor 540 in perspective view. FIG. 5C shows the lead anchor 540 in side view. The lead anchor 540 includes a central body 542 that includes a twistable region 558 and that defines a lead passageway 552. The twistable region 558 is flanked by a first hub 564 and a second hub 566 that are attached to lateral ends of the central body 542 such that rotation of one of the hubs 564, 566 relative to the other causes a corresponding twisting (or untwisting) of the twistable region 558. In at least some embodiments, the lead passageway extends through at least one of the hubs 564, 566. In the illustrated embodiment, the lead passageway is shown extending through both hubs 564, 566. The twistable region 558 can extend along the entire longitudinal length of the central body 542, or along less than the entire longitudinal length of the central body 542. The twistable region 558 is flexible enough to be twistable and stretchable along the longitudinal length of the central body 542.

Transitioning the hubs 564, 566 from a locked position to an unlocked position can be performed by stretching the twistable region 558 by an amount sufficient to disengage the locking member from at least one of the hubs. In at least some embodiments, stretching the twistable region 558 can be performed by pulling the hubs 564, 566 apart from one another along the longitudinal length of the central body. Conversely, transitioning the hubs 564, 566 from an unlocked position to a locked position can be performed by stretching the twistable region 558 by an amount sufficient to engage the locking member with both hubs.

The lead anchor 540 includes a locking mechanism 576 with a locking member 577 suitable for engaging the hubs 564, 566 and enabling the hubs 564, 566 to be transitioned between an unlocked position and a locked position. The locking member 577 illustrated in FIGS. 5A-5C includes a central tube 588 that fits concentrically around the central body 542 and that engages with the hubs 564, 566 to prevent rotation of the hubs relative to one another. In some embodiment, the hubs are both removably attached to the central tube. In alternate embodiments, one of the hubs is removably attached to the central tube and the other hub is permanently attached to the central tube.

The central tube 588 can engage with one or more of the hubs 564, 566 in a variety of different ways, including by engagement surfaces that interlock with one another to resist rotation relative when coupled together. In the illustrated embodiment, the engagement surfaces are formed as sets of interlocking tabs and notches that removably couple the hubs to the central body. In FIGS. 5A-5C, lateral edges of the central tube 588 define notches 590, 590' configured to receive tabs 592, 592', respectively, which extend from medial edges of the hubs 564, 566, respectively. In FIGS. 5A-5C, two circumferentially-opposed sets of interlocking notches and tabs are shown along each hub-central tube interface. It will be understood that any suitable number of sets of interlocking notches and tabs can be used along each hub-central tube interface including, for example, one, two, three, four, five, six, seven, eight, or more sets of notches and interlocking tabs. In FIGS. 5A-5C, for each interlocking set of notches and tabs, the notches are shown defined in the central tube and the tabs disposed on the hubs. In alternate embodiments, for each interlocking set of notches and tabs, the notches are shown defined in the hub and the tabs disposed on the central tube. In other alternate embodiments, the central tube defines at least one notch and includes at least one tab, where the notch is suitable for receiving a tab disposed on one of the hubs, and the at least one tab is suitable for being received by a notch defined along one of the hubs.

The interlocking engagement surfaces are suitable for preventing rotation of the central tube relative to the hubs when mated together (i.e., in the locked position). The lead anchor can be transitioned from the locked position to the unlocked position by axially moving at least one of the hubs relative to the central tube enough to remove the tabs from their respective notches. Once unlocked, the hubs can be rotated relative to one another, as described above with reference to FIG. 3B.

The central tube 588 can be formed from any suitable implantable material (e.g., metal, alloy, polymer) that is more rigid than the twistable region 458. Optionally, the central tube 588 defines at least one slot, such as slot 594, for facilitating flexing and bending and providing strain relief. The slot(s) 594 extend circumferentially in a direction that is transverse, or approximately transverse, to a longitudinal length of the central tube.

Optionally, the lead anchor 540 can include one or more optional protruding features with eyelets for receiving a suture, a staple, or the like, for securing the lead anchor 540 to patient tissue (see e.g., protruding features 280 and eyelets 282 of FIGS. 2A-2B). In at least some embodiments, the central body 542 includes one or more optional suture channel that are disposed at least partially around a circumference of the central body 542 (see e.g., suture channels 284 of FIGS. 2A-2B).

Figure 6A:
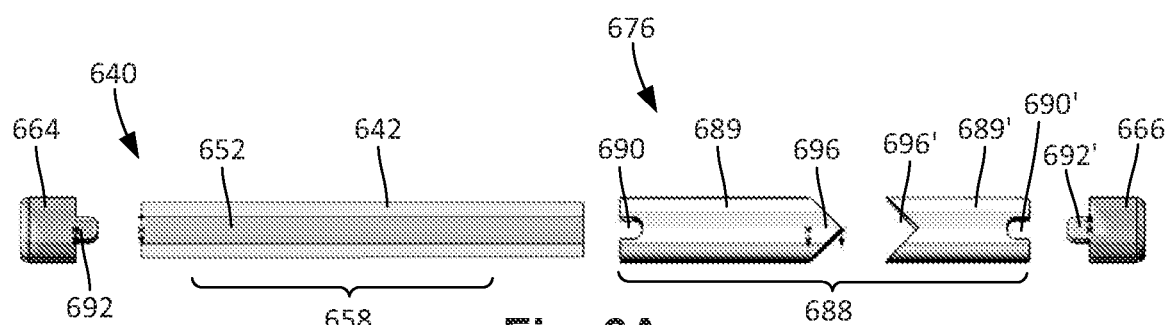
FIG. 6A is a schematic exploded view of yet another embodiment of a lead anchor suitable for use with the lead or lead extension of FIG. 1, according to the invention.
Figure 6B:
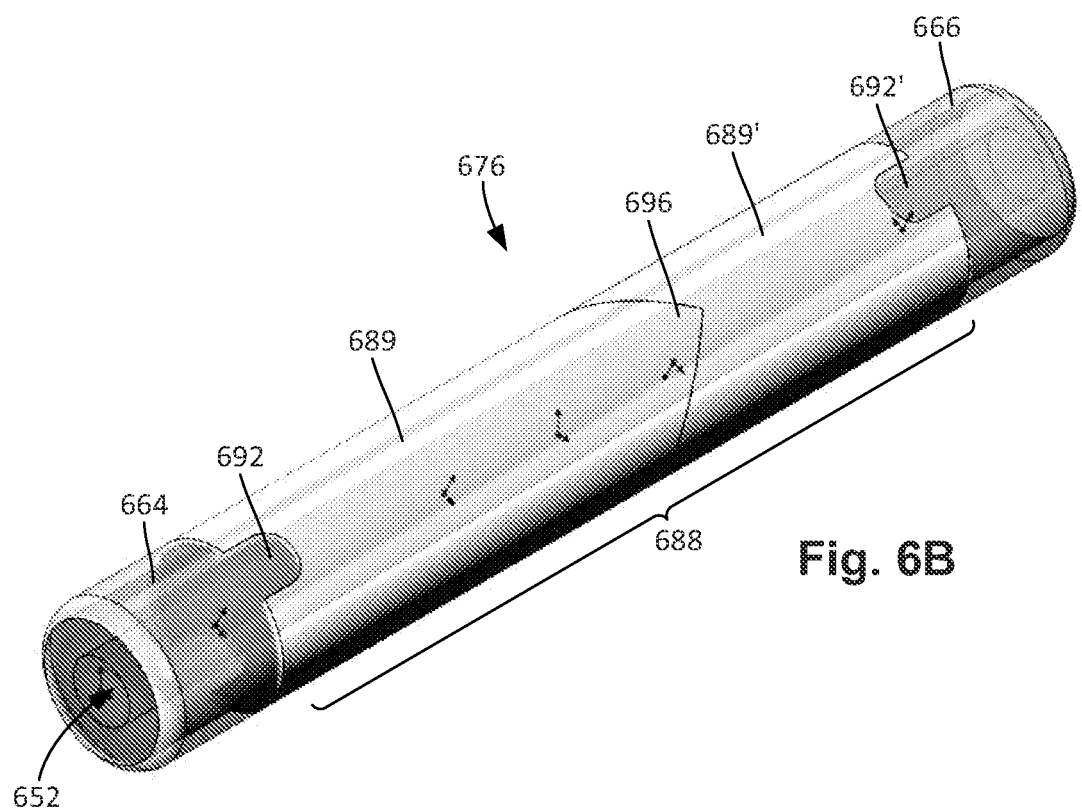
FIG. 6B is a schematic perspective view of one embodiment of the lead anchor of FIG. 6A, according to the invention.
Figure 6C:
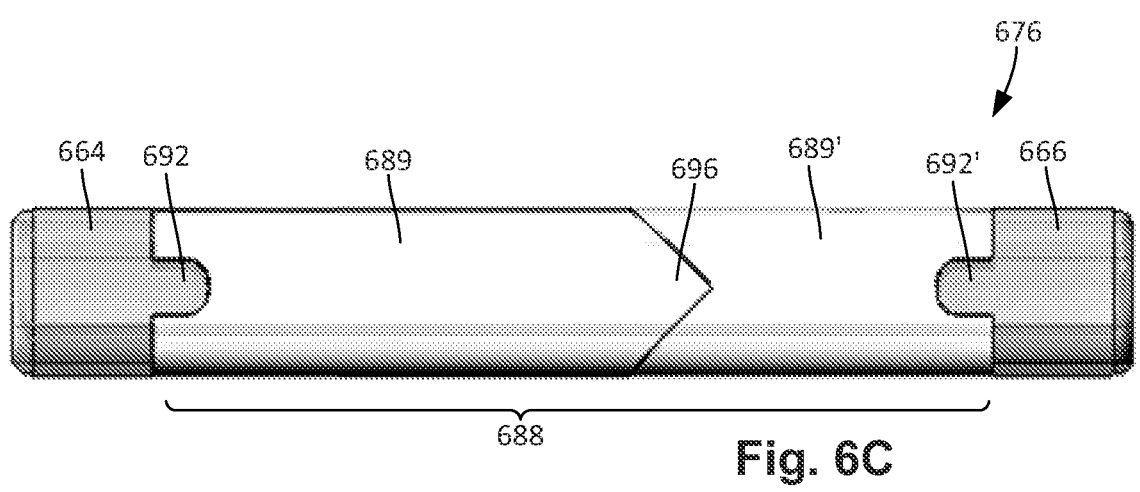
FIG. 6C is a schematic side view of one embodiment of the lead anchor of FIG. 6A, according to the invention.

FIGS. 6A-6C illustrates a third embodiment of a locking mechanism of a lead anchor 640 suitable for anchoring to a lead. FIG. 6A shows the lead anchor 640 in exploded side view. FIG. 6B shows the lead anchor 640 in perspective view. FIG. 6C shows the lead anchor 640 in side view. The lead anchor 640 includes a central body 642 that includes a twistable region 658 and that defines a lead passageway 652. The twistable region 658 is flanked by a first hub 664 and a second hub 666 that is attached to lateral ends of the central body 642 such that rotation of one of the hubs 664, 666 relative to the other causes a corresponding twisting (or untwisting) of the twistable region 658. In at least some embodiments, the lead passageway extends through at least one of the hubs 664, 666. In the illustrated embodiment, the lead passageway is shown extending through both hubs 664, 666. The twistable region 658 can extend along the entire longitudinal length of the central body 642, or along less than the entire longitudinal length of the central body 642. The twistable region 658 is flexible enough to be twistable and stretchable along the longitudinal length of the central body 642.

Transitioning the hubs 664, 666 from a locked position to an unlocked position can be performed by stretching the twistable region 658 by an amount sufficient to disengage the locking member from at least one of the hubs. In at least some embodiments, stretching the twistable region 658 can be performed by pulling the hubs 664, 666 apart from one another along the longitudinal length of the central body. Conversely, transitioning the hubs 664, 666 from an unlocked position to a locked position can be performed by stretching the twistable region 658 by an amount sufficient to engage the locking member with both hubs.

The lead anchor 640 includes a locking mechanism 676 with a locking member 677 suitable for engaging the hubs 664, 666 and enabling the hubs 664, 666 to be transitioned between an unlocked position and a locked position. The locking member 677 illustrated in FIGS. 6A-6C includes a central tube 688 that can be separated into multiple components and that fits concentrically around the central body 642. In the illustrated embodiments, the central tube 688 includes a first interlocking member 689 that mates with a second interlocking member 689' along interlocking engagement surfaces to resist rotation of the hubs 664, 666 when the interlocking members 689, 689' are mated. The first interlocking member 689 couples with the first hub 664, and the second interlocking member 689' couples with the second hub 666.

In some embodiment, the hubs can be transitioned from an unlocked position to a locked position by disengaging interlocking engagement surfaces between: the interlocking members 689, 689'; between the first interlocking member 689 and the first hub 664; between the second interlocking member 689' and the second hub 666; or some combination thereof.

The first interlocking member 689 mates to the second interlocking member 689' along interlocking engagement surfaces. In the illustrated embodiment, the engagement surfaces of the interlocking members 689, 689' include a projection 696 disposed along the first interlocking member 689, and a correspondingly-shaped recess 696' defined along the second interlocking member 689'. In alternate embodiments, the projection 696 is disposed along the second interlocking member 689' and the recess 696' is defined along the first interlocking member 689.

In FIGS. 6A-6C, one set of interlocking engagement surfaces is shown disposed along the interface between the interlocking member 689, 689'. It will be understood that any suitable number of sets of interlocking engagement surfaces can be used along the interface between the interlocking member 689, 689' including, for example, one, two, three, four, five, six, seven, eight, or more sets.

The interlocking surfaces can be formed in any shape sufficient to resist rotational movement of the first interlocking member 689 relative to the second interlocking member 689' when the interlocking surfaces are mated. In the illustrated embodiment, the interlocking surfaces are V-shaped. Other shapes are possible in lieu of, or in addition to, V-shaped interlocking surfaces including, for example, U-shaped surfaces, or irregularly-shaped surfaces. In at least some embodiments, the interlocking surfaces may include a continuous pattern with multiple repeating shapes, such as a saw-tooth, a sine-wave, or a combination of both.

In some embodiment, the hubs 664, 666 are both removably attached to the central tube 688. In alternate embodiments, one of the hubs 664, 666 is removably attached to the central tube 688 and the other hub 664, 666 is permanently attached to the central tube 688. In at least some embodiments, the hubs 664, 666 are both permanently attached to the central tube 688. When the central tube 688 is removably attached to one, or both, of the hubs 664, 666, the central tube 688 can engage the hubs 664, 666 in a similar manner as described above, with reference to FIGS. 5A-5C.

The central tube 688 can be formed from any suitable implantable material (e.g., metal, alloy, polymer) that is more rigid than the twistable region 658. Optionally, the central tube 688 defines at least one slot extending circumferentially (see e.g., slot 594 of FIGS. 5A-5C) the central tube for facilitating flexing and bending and providing strain relief.

Optionally, the lead anchor 640 can include one or more optional protruding features with eyelets for receiving a suture, a staple, or the like, for securing the lead anchor 640 to patient tissue (see e.g., protruding features 280 and eyelets 282 of FIGS. 2A-2B). In at least some embodiments, the central body 642 includes one or more optional suture channel that are disposed at least partially around a circumference of the central body 642 (see e.g., suture channels 284 of FIGS. 2A-2B).

Figure 7A:
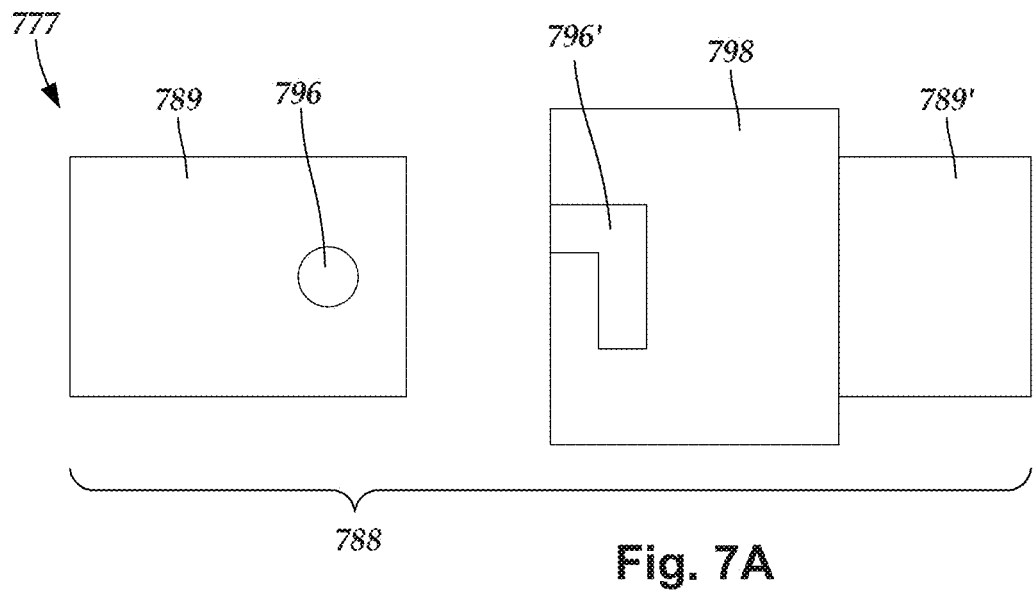
FIG. 7A is a schematic exploded view of an alternate embodiment of a locking member in an unlocked position, the locking member suitable for use with the lead anchor of FIGS. 6A-6C, according to the invention.
Figure 7B:
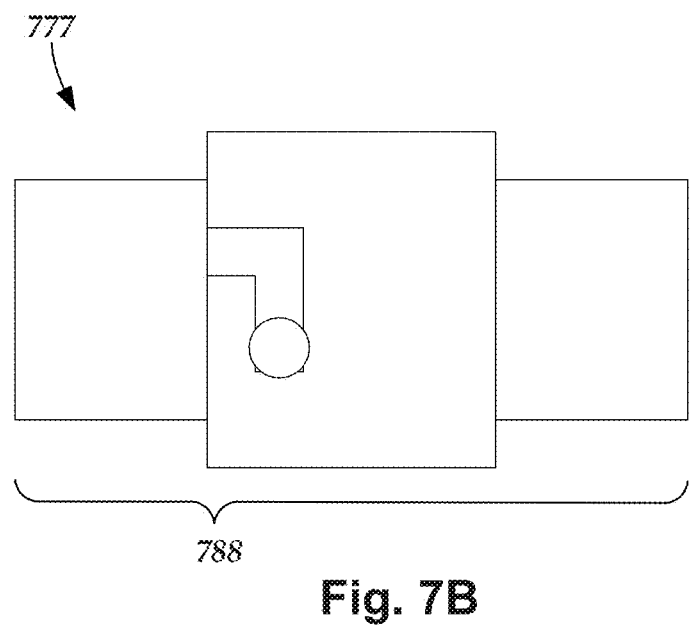
FIG. 7B is a schematic side view of one embodiment of the locking member of FIG. 7A in a locked position, according to the invention.

FIGS. 7A-7B illustrates a fourth embodiment of a locking member 777 suitable for disposing along a lead anchor. FIG. 7A shows the locking member 777 in exploded side view. FIG. 7B shows the locking member 777 in side view. The locking member 777 is similar to the locking member 677, but with different interlocking engagement surfaces.

The locking member 777 is suitable for enabling hubs of a lead anchor to be transitioned between an unlocked position and a locked position. The locking member 777 illustrated in FIGS. 7A-7B includes a central tube 788 that can be separated into multiple components and that fits concentrically around a central body (not shown). In the illustrated embodiments, the central tube 788 includes a first interlocking member 789 that interlocks with a second interlocking member 789' along interlocking engagement surfaces to resist rotation of the coupled hubs (not shown) when the tube portions 789, 789' are mated.

The first interlocking member 789 mates to the second interlocking member 789' along interlocking engagement surfaces. In the illustrated embodiment, the engagement surfaces include a knob 796 disposed along the first interlocking member 789, and a correspondingly-dimensioned groove 796' defined extending from an end of the second interlocking member 789'. In alternate embodiments, the knob 796 is disposed along the second interlocking member 789' and the groove 796' is defined along the first interlocking member 789.

In the illustrated embodiment, the groove 796' includes a bend. Consequently, in at least some embodiments, engagement of the knob 796 with the groove 796' includes twisting at least one of the first interlocking member 789 or the second interlocking member 789' relative to the other when the knob 796 is partially inserted into the groove 796' to lock the hubs. In at least some embodiments, interlocking the engagement surfaces involves partial insertion of the interlocking member 789, 789' upon which the knob 796 is disposed into the interlocking member 789, 789' upon which the groove 796' is defined. In which case, at least a portion of the interlocking member 789, 789' upon which the groove 796' is defined has a larger diameter than the interlocking member 789, 789' upon which the knob 796 is disposed. In FIGS. 7A-7B, the interlocking member 789' upon which the groove 796' is defined has an interlocking region 798 with a diameter sufficient to receive an end of the interlocking member 789, 789' upon which the knob 796 is disposed.

The central tube 688 can be formed from any suitable implantable material (e.g., metal, alloy, polymer) that is more rigid than the twistable region 658. Optionally, the central tube 688 defines at least one slot extending circumferentially (see e.g., slot 594 of FIGS. 5A-5C) the central tube for facilitating flexing and bending and providing strain relief.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor comprising:
   a central body having a longitudinal length with a first end portion and an opposing second end portion, wherein the central body is made of a polymeric material that can be twisted and stretched, wherein the central body comprises a twistable region extending along at least a portion of the longitudinal length of the central body with a lead passageway extending therethrough, the twistable region configured and arranged for reversibly twisting and stretching along the longitudinal length of the central body;
   the lead passageway having a cylindrical wall defined by the central body and extending along the entire longitudinal length of the central body, the lead passageway configured and arranged to receive a lead;
   a first hub coupled to the central body along the first end portion of the central body;
   a second hub coupled to the central body along the second end portion of the central body and separated from the first hub by the central body, wherein the first hub is rotatable relative to the second hub about the central body, the rotation of the first hub relative to the second hub causing a corresponding twisting of the twistable region from an untwisted configuration into a twisted configuration, wherein when a lead is inserted into the lead passageway and the twistable region is twisted into the twisted configuration the central body compresses against an outer surface of the lead to retain the lead within the lead passageway; and
   a locking mechanism that comprises at least one locking member configured and arranged to transition the first hub and the second hub between an unlocked position where the first hub is rotatable relative to the second hub and a locked position where the first hub and the second hub resist rotation relative to one another; wherein the at least one locking member comprises a plurality of pins disposed externally to the central body, wherein the first hub and the second hub are each configured to receive at least a portion of each of the pins.

2. The lead anchor of claim 1, wherein the locking mechanism is configured and arranged to transition the first hub and the second hub from the unlocked position to the locked position by physical engagement of the first hub and the second hub using the at least one locking member.

3. The lead anchor of claim 1, wherein the locking mechanism is configured and arranged to transition the first hub and the second hub from the locked position to the unlocked position by physical disengagement of the at least one locking member from at least one of the first hub or the second hub.

4. The lead anchor of claim 1, wherein the twistable region is disposed entirely between the first hub and the second hub.

5. The lead anchor of claim 1, wherein the twistable region comprises at least one bump to provide localized resistance against patient tissue.

6. The lead anchor of claim 1, further comprising at least one protruding feature attached to the central body and defining an eyelet configured and arranged for receiving a suture.

7. The lead anchor of claim 6, further comprising at least one suture channel disposed at least partially around a circumference of the central body and aligned axially along the longitudinal length of the central body with the at least one protruding feature.

8. An implantable stimulation arrangement, comprising:
the lead anchor of claim 1; and
an electrical stimulation lead comprising an electrode array, wherein the lead anchor is configured and arranged for receiving a portion of the electrical stimulation lead and removably retaining the received portion of the electrical stimulation lead.

9. An implantable stimulation device, comprising:
the lead anchor of claim 1;
an electrical stimulation lead comprising an electrode array and coupleable to the lead anchor; and
a control module coupleable to the electrical stimulation lead.

10. A method of anchoring a lead, comprising:
providing the lead anchor of claim 1;
advancing an electrode array of an electrical stimulation lead into a patient to a target stimulation location;
sliding the lead anchor along the electrical stimulation lead to a desired placement position along the electrical stimulation lead with a portion of the electrical stimulation lead disposed within the lead passageway of the lead anchor;
twisting the twistable region to hold the electrical stimulation lead in position relative to the lead anchor; and
transitioning the locking mechanism to the locked position to prevent the twistable region from untwisting.

11. The method of claim 10, further comprising transitioning the locking mechanism of the lead anchor to the unlocked position prior to twisting the twistable region.

12. The method of claim 10, wherein twisting the twistable region to hold the electrical stimulation lead in position relative to the lead anchor comprises rotating the first hub relative to the second hub about the longitudinal length of the central body of the lead anchor.

* * * * *